US009212979B2

(12) United States Patent
Chanbasha et al.

(10) Patent No.: US 9,212,979 B2
(45) Date of Patent: Dec. 15, 2015

(54) AUTOMATED MICROEXTRACTION TECHNIQUE FOR THE ANALYSIS OF N-NITROSAMINES IN WATER

(71) Applicants: King Fahd University of Petroleum and Minerals, Dhahran (SA); King Abdulaziz City for Science and Technology, Riyadh (SA)

(72) Inventors: Basheer Chanbasha, Dhahran (SA); Mousa Yaser Amayreh, Dhahran (SA)

(73) Assignees: King Fahd University of Petroleum and Minerals, Dhahran (SA); King Abdulaziz City for Science and Technology, Riyadh (SA)

( * ) Notice: Subject to any disclaimer, the term of this patent is extended or adjusted under 35 U.S.C. 154(b) by 0 days.

(21) Appl. No.: 14/155,429

(22) Filed: Jan. 15, 2014

(65) Prior Publication Data
US 2015/0198574 A1  Jul. 16, 2015

(51) Int. Cl.
*G01N 30/88* (2006.01)
*G01N 1/40* (2006.01)
*G01N 30/06* (2006.01)
*H01J 49/04* (2006.01)
*B01D 53/02* (2006.01)
*G01N 30/72* (2006.01)
*G01N 30/00* (2006.01)

(52) U.S. Cl.
CPC .............. *G01N 1/405* (2013.01); *B01D 53/025* (2013.01); *G01N 30/06* (2013.01); *G01N 30/88* (2013.01); *H01J 49/0431* (2013.01); *G01N 30/7206* (2013.01); *G01N 2030/009* (2013.01); *G01N 2030/062* (2013.01); *G01N 2030/8804* (2013.01); *G01N 2030/8813* (2013.01)

(58) Field of Classification Search
CPC ............ G01N 1/405; G01N 2030/062; G01N 2035/1053; G01N 2030/025; H01J 49/0431
See application file for complete search history.

(56) References Cited

U.S. PATENT DOCUMENTS

| 3,996,008 | A | 12/1976 | Fine et al. |
| 6,825,046 | B1 | 11/2004 | Forsyth |
| 2006/0162008 | A1* | 7/2006 | Green et al. ................. 800/278 |
| 2012/0264227 | A1* | 10/2012 | Couch ........................ 436/173 |

OTHER PUBLICATIONS

Llop et al., "Fully automated determination of N-nitrosamines in environmental waters by headspace solid-phase microextraction followed by GC-MS-MS", J.Sep. Sci. 2010, 33, 3692-3700.*
Modir-Rousta et al., "New pressure-assisted sweeping on-line preconcentration for polar environmentally relevant nitrosamines: Part 1. Sweeping for polar compounds and application of auxiliary pressure", Electrophoresis 2013, 34, 2553-2560.*

(Continued)

*Primary Examiner* — Michael Logie
(74) *Attorney, Agent, or Firm* — Oblon, McClelland, Maier & Neustadt, L.L.P.

(57) ABSTRACT

An automated headspace solid-phase microextraction coupled with gas chromatography-mass spectrometry for the determination of four N-nitrosamines in groundwater samples is developed. Response surface methodology technique was employed to investigate the optimized extraction conditions of headspace solid-phase microextraction using CombiPAL autosampler. The method was applied to determine the N-nitrosamine concentrations in groundwater samples.

8 Claims, 6 Drawing Sheets

(56) References Cited

OTHER PUBLICATIONS

Application Note 17, "Polyacrylate film fiber for solid phase microextraction of Polar Semivolatiles from Water", Sigma-Aldrich Co., 1998.*

Llop et al. "Auotmated on-fiber derivatization with headspace SPME-GC-MS-MS for the determination of primary amines in sewage sludge using pressurized hat water extraction", J. Sep. Sci. 2011,34, 1531-1537.*

Qiu et al., "Optimization of the Headspace Solid-Phase Microextraction Gas Chromatography for Volatile Compounds Determination in Phytophthora Cinnamomi Rands", World Academy of Science, Engineering and Technology vol. 6 2012.*

Method 8070A, "Nitrosamines by Gas Chromatography", Revision Dec. 1, 1996.*

Wang et al., "Derivatization Method for Determination of Nitrosamines by GC-MS", Chromatographia (2011).*

"Derivatization Method for Determnation of Nitrosamines by GC-MS", Wang, X Article, Fudan Univ Feb. 2011, Chromatographia 73 (3-4), 321-327. (Abstract Only) 1 page.

"Trace Analysis of N-Nitrosamines in Water Using Solid-Phase Microextraction Coupled With Gas Chromatograph-TANDEM Mass Spectrometry" Hung, HW Article Natl Cheng Kung Univ., Nov. 2010, Water Air and Soil Pollution 213 (1-4): 459-469, (Abstract Only) 1 page.

"Solid-Phase Microextraction of N-Nitrosamines", Grebel JE Article, Univ Calif, Los Angeles, Jun. 2, 2006, Journal of Chromatography A 1117 (1): 11-18, (Abstract Only) 1 page.

\* cited by examiner

AUTOMATED MICROEXTRACTION TECHNIQUE FOR THE ANALYSIS OF N-NITROSAMINES IN WATER

BACKGROUND OF THE INVENTION

1. Technical Field

The present invention relates to an automated headspace solid-phase microextraction coupled with gas chromatography-mass spectrometry method for determining nitrosamine concentration using a polyacrylate fiber.

2. Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

N-nitrosamines (NAs) are a class of organic compounds derived from the reaction of amines (secondary amines) with nitrosating agents (Llop, A., Borrull, F., Pocurull, E., J. Sep. Sci. 2010, 33, 3692-3700.4; Llop, A., Pocurull, E., Borrull, F., J. Chromatogr. A 2010, 1217, 575-581—each incorporated herein by reference in its entirety). NAs are classified as potentially hazardous disinfection by-products (DBPs) produced through a chlorine based disinfection processes of drinking water (Wang, W., Ren. S., Zhang, H., Yu. Y., An. W., Hu. J., Yang. M., Water Res. 2011, 45, 4930-4938—incorporated herein by reference in its entirety). NAs were also present in other anthropogenic source such as polymer waste, plasticizers, rocket fuel (incomplete oxidation of hydrazines), batteries and other industrial products.

As a result, NAs were detected in wide ranges of sample matrices which includes drinking, ground, waste and treated wastewater samples (Anna, V., Rimma, S., Ovadia, L., Jenny, G., Anal. Chim. Acta. 2011, 685, 162-169; Richardson, S. D., Anal. Chem. 2009, 81, 4645-4677—each incorporated herein by reference in its entirety), soils (Pan, X., Zhang, B., Cox, S. B., Anderson, T. A., Cobb, G. P., J. Chromatogr. A 2006, 1107, 2-8—incorporated herein by reference in its entirety), cosmetics (Qiang, M., Hai-Wei, X., Chao, W., Hua, B., Guang-Cheng, X., Ning, S., Li-Yan, X., Jun-Bing, W., Chin. J. Anal. Chem. 2011, 39, 1201-1207; Schothorst, R. C., Somers, H. H. J., Anal. Bioanal. Chem. 2005, 381, 681-685; Flower, C., Carter, S., Earls, A., Fowler, R., Hewlins, S., Lalljie, S., Lefebvre, M., Mavro, J., Small, D., Volpe, N., Int. J. Cosmet. Sci. 2006, 28, 21-33—each incorporated herein by reference in its entirety), biological sample (urine, saliva, blood), tobacco smoke (Ramrez, N., Ozel, M., Lewis, A., Marce, M., Borrull, F., Hamilton, J. Chromatogr. A 2012, 1219, 180-187—incorporated herein by reference in its entirety). Trace amounts of NAs were detected in many food products such as bacon (Ventanas S, Ruiz. J., Talanta 2006, 70, 1017-1023—incorporated herein by reference in its entirety), fish and beer (Sanches, P. J. F., Zanin, K. E., Camarão, E. B., Garcia, R. C., Rios, A., Valcarcel, M., Quimica Nova 2003, 193-196; Mendez, D., Gonzalez, G., Botello, E., Escamilla, E., Alvarado, J. F. J., Food Chem. 2008, 107, 1348-1352—each incorporated herein by reference in its entirety) meat (Campillo, N., Vinas, P., Martnez-Castillo, N., Hernndez-Crdoba, M., J. Chromatogr. 2011, 1218, 1815-1821—incorporated herein by reference in its entirety), and frankfurters and sausages (Oliveira, C. P., Gloria, M. B. A., Barbuor, J., Scalan, R. A., J. Agric. Food Chem. 1995, 43, 967-969—incorporated herein by reference in its entirety).

NAs are receiving special attention due to high toxicity effects and due to the ability to enhance tumors in various animal and human species (Yurchenko, S., Molder, U., Food Chem. 2006, 96, 325-333; Andrade, R., Reyes, F. G. R., Rath, S., Food Chem. 2005, 91, 173-179; Andrade, R., Reyes, F. G. R., Rath, S., Food Chem. 2005, 91, 173-179—each incorporated herein by reference in its entirety). International Agency for Research on Cancer (IARC) and the US Environmental Protection Agency (USEPA) listed NAs as potentially carcinogenic to humans (Kaserzon, S. L., Kennedy, K., Hawker, D. W., Holling, N., Escher, B. I., Booij, K., Mueller, J. F., Chemosphere 2011, 84, 497-503; Boyd, J. M., Hrudey, S. E., Richardson, S. D., Li, X. F., Trends in Analytical Chemistry 2011, 30, 1411-1421—each incorporated herein by reference in its entirety). The USEPA has established the control level (ng/L) of NAs in drinking water (Llop, A., Borrull, F., Pocurull, E., Talanta 2012, 88, 284-289; Fiddler, W., Pensabene, J. W., & Kimoto, W. L., J. Food Sci. 1981, 46, 603-605—each incorporated herein by reference in its entirety).

The most common analytical methods have been used for determination of NAs are (i) colorimetry (Jurado-Sanchez, B., Ballesteros, E., Gallego, M., Talanta 2007, 73, 498-504—incorporated herein by reference in its entirety), (ii) capillary electro-chromatography (CE) (Matyska, M. T., Pesek, J. J., Yang, L., J. Chromatogr. A 2000, 887, 497-503—incorporated herein by reference in its entirety), (iii) micellar electrokinetic capillary chromatography (MECC) (Filho, P. J. S., Rios, A., Valcarcel, M., Caramao, E. B., Water Res. 2003, 37, 3837-3842—incorporated herein by reference in its entirety), (iv) gas chromatography (GC) with different detector such as flame ionization detector (FID) (Jurado-Sanchez, B., Ballesteros, E., Gallego, M., J. Chromatogr A, 2007, 1154, 66-73—incorporated herein by reference in its entirety), nitrogen phosphorous detector (NFD) (Andrade, R., Reyes, F. G. R., Rath, S., Food Chem. 2005, 91, 173-179—incorporated herein by reference in its entirety), thermal energy detector (TED) (Incavo, J. A., Schafer, M. A., Anal. Chim. Acta, 2006, 557, 256-261—incorporated herein by reference in its entirety), nitrogen chemiluminescence detector (NCI)) (Ozel, M. Z., Gogus, F., Yagci, S., Hamilton, J. F., Lewis, A. C., Food Chem. Toxicol. 2010, 48, 3268-3273—incorporated herein by reference in its entirety) and with mass spectrometry detector (MSD) (Anna, V., Rimma, S., Lev, O., Jenny, G., Anal. Chim. Acta. 2011, 685, 162-169—incorporated herein by reference in its entirety). Recently, high-performance liquid chromatography (HPLC) methods with different detectors MSD (Xiong W, Hou H W, Jiang X Y, Tang G L, Hu Q Y. Anal. Chim. Acta, 2010, 674(1): 71-78—incorporated herein by reference in its entirety), ultra violet detector (UVD) (Kodamatani, H., Yamazaki, S., Saito, K., Amponsaa-Karikari, A., Kishikawa, N., Kuroda, N., Tomiyasu, T., Komatsu, Y., J. Chromatogr. A 2009, 1216, 92-98—incorporated herein by reference in its entirety), and fluorescence detectors (FD) (Zhao, Y.-Y., Boyd, J., Hrudey, S. E., Li, X.-F., Environ. Sci. Technol. 2006, 40, 7636-7641—incorporated herein by reference in its entirety) were used for the analysis of NAs. Analysis of NAs by using GC is more sensitive than HPLC methods (Krauss, M., Hollender, J., Anal. Chem. 2008, 80, 834-842; Plumlee, M., Ló pez-Mesas, M., Heidlberger, A., Ishida, K. P., Reinhard, M., Water Res. 2008, 42, 347-355—incorporated herein by reference in its entirety).

The most common preconcentrating techniques used for NAs in water samples are solid-phase extraction (SPE) with sorbent materials such as carbonaceous Ambersorb-572 and coconut charcoal (Perez, D. M., Alatorre, G. G., Alvarez, E. B., Silva, E. E., Alvarado, J. F. J., Food Chem. 2008, 107, 1348-1352; Planas, C., Palacios, O., Ventura, F., Rivera, J., Caixach, J., Talanta 2008, 76, 906-913—each incorporated herein by reference in its entirety). Alternatively, liquid-liquid extraction (LLE) (Raksit, A., Johri, S., J. AOAC Int. 2001, 84, 1413-1419—incorporated herein by reference in its entirety) was also reported, however, LLE consumes large amounts of organic solvents and is not easy to automate the extraction procedure. Solid-phase microextraction (SPME) (Ventanas, S., Ruiz, J., Talanta 2006, 70, 1017-1023; Grebel, J. E., Young, C. C., Suffet, I. H., J. Chromatogr. A 2006, 1117, 11-18—each incorporated herein by reference in its entirety), which is a solvent-free and more environmentally friendly method is easy to automate using CombiPAL autosampler.

Automated-SPME has more advantages such as a high degree of accuracy and reproducibility compared to the conventional approach. Herein is disclosed the development of a simple automated HS-SPME method using CombiPAL autosampler for the first time for the determination of NAs. Various extraction parameters influencing the performance of HS-SPME such as different type of commercial fibers, extraction time, sample pH, incubation temperature and ionic strength of the aqueous solution were determined using Response Surface Methodology (RSM).

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

One embodiment of the disclosure includes an automated headspace solid-phase microextraction (SPME) method coupled with gas-chromatography-mass spectrometry.

In another embodiment the method is used to determine N-nitrosamine concentration in a sample.

In another embodiment the method further includes extracting an analyte composition from an aqueous solution sample by contacting the aqueous solution sample with an SPME fiber and placing the analyte-enriched SPME fiber into an injection port of a gas chromatograph.

In another embodiment the method further includes desorbing a nitrosamine-containing analyte from the analyte-enriched SPME fiber and chromatographing the nitrosamine-containing analyte in the gas chromatograph to determine the nitrosamine content in the nitrosamine-containing analyte.

In another embodiment the SPME fiber is a polyacralyte fiber.

In another embodiment the aqueous solution is mixed with one or more salts before extraction.

In another embodiment no derivization of the nitrosamine content is carried out.

In another embodiment automated headspace analysis is used as a gas chromatographic technique.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings wherein.

DETAILED DESCRIPTION OF THE EMBODIMENTS

Figure 1:
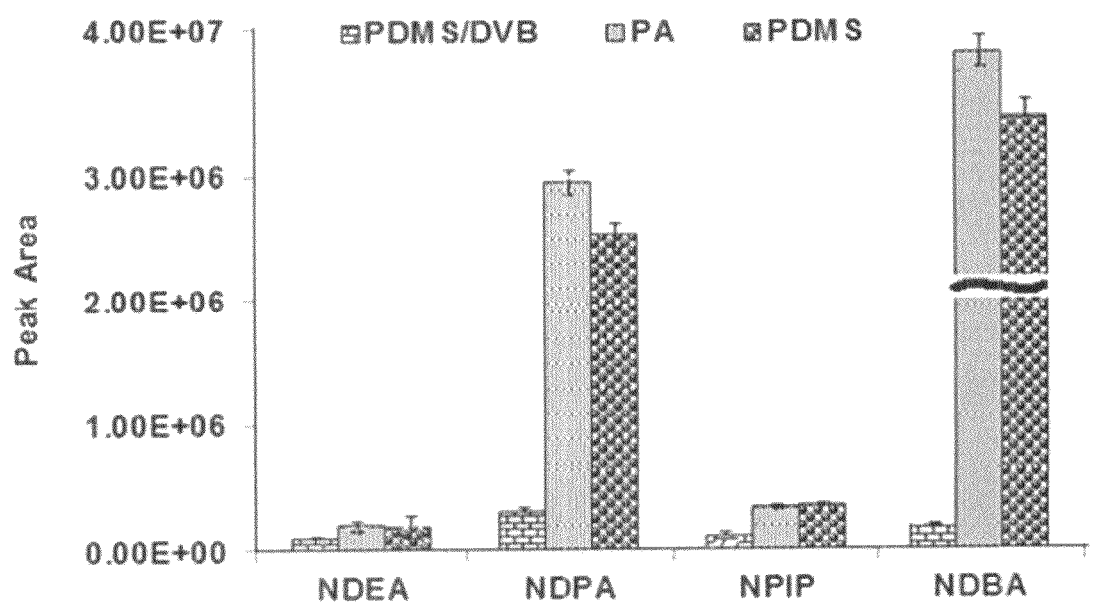
FIG. 1 is a graph of a comparison of different SPME fibers.
Figure 2A:
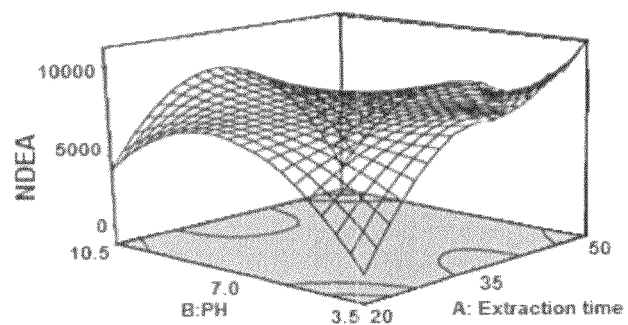
FIGS. 2A-2D are diagrams that illustrate the influence of extraction time and sample pH on HS-SPME.
Figure 2B:
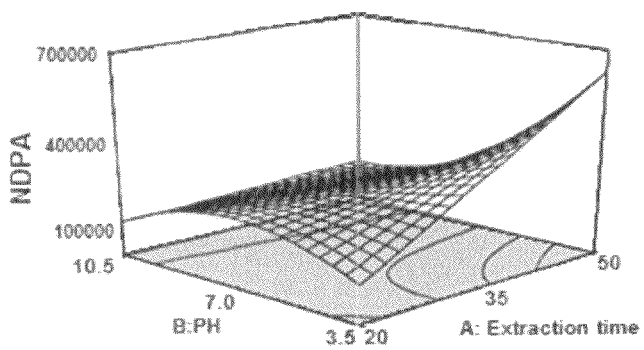
Figure 2C:
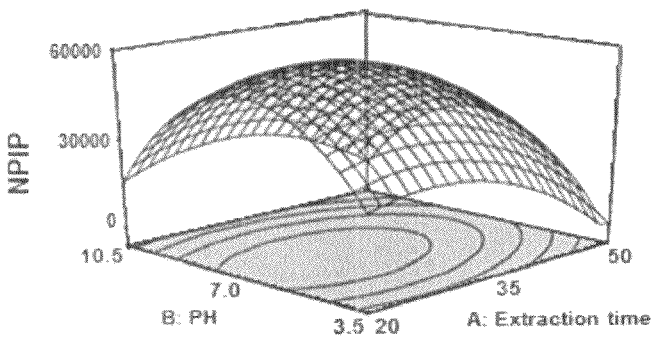
Figure 2D:
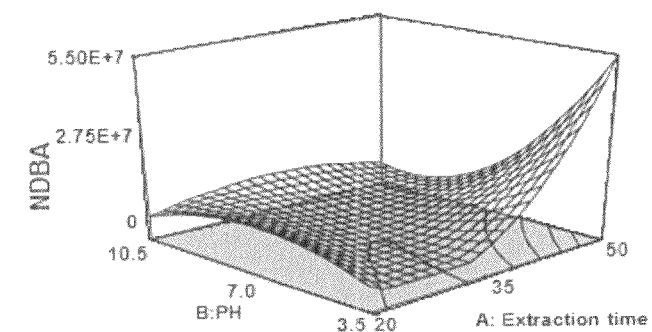
Figure 3A:
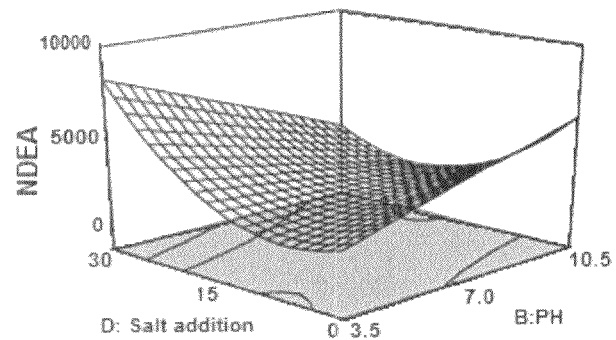
FIGS. 3A-3D are diagrams that illustrate the effect of sample pH and salt addition on HS-SPME.
Figure 3B:
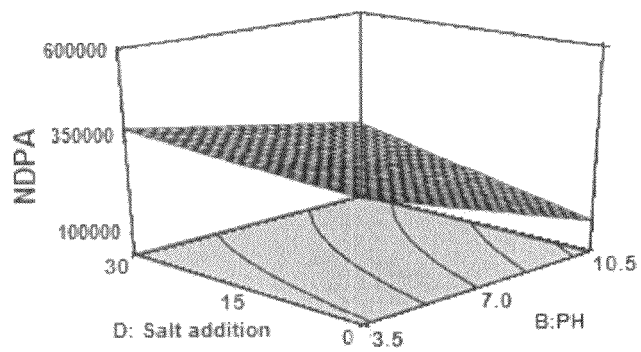
Figure 3C:
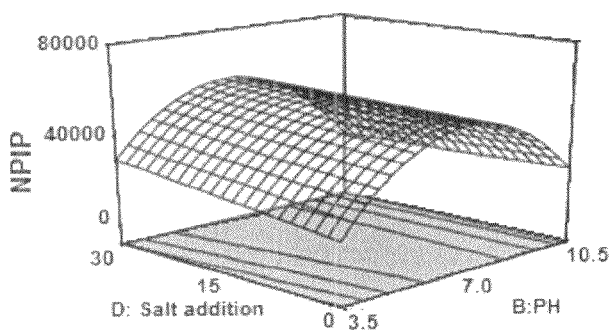
Figure 3D:
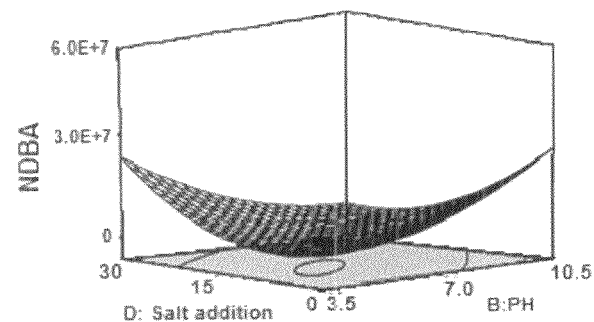

Referring now to the drawings, wherein like reference numerals designate identical or corresponding parts throughout the several views.

The disclosure includes a method in which an aqueous sample is analyzed for nitrosamine content. In the method an aqueous sample is analyzed for nitrosamine-containing content. The nitrosamine content is preferably in the range of 0.1 to 100 µg/L, e.g., 0.1, 1, 5, 10, 20, 30, 50, or 100 µg/L. Prior to analysis the aqueous sample may be handled and prepared using manual methods of mixing including but not limited to swirling the solution by hand and by placing a magnetic stir bar in the solution and stirring with a magnetic stir plate. Mechanical methods include but are not limited to sonicating the solution using an ultrasonic bath or an ultrasonic probe or ultrasonicating the solution. Preferably, swirling the solution by hand is used.

The aqueous sample used for analysis typically contains a volume of 2-20 mL, 3-15 mL, or 4-10 mL water. Preferably a volume of 5 mL aqueous sample is used. The pH of the aqueous sample mixed with nitrosamine-content is adjusted within a pH range of 6-8. Preferably, the pH of the aqueous sample mixed with nitrosamine-content has a pH of 7.

Preferably the sample is poured into a head space solid-phase microextraction (HS-SPME) vial containing a salt in the range of 0.05-0.25 g, 0.10-0.20 g, or 0.14-0.19 g and/or a SPME fiber. The salt includes but is not limited to salts such as sodium chloride (NaCl), sodium bisulfate (NaHSO$_4$), or calcium chloride (CaCl$_2$). Salts of other alkali and alkaline earth metals such as potassium and magnesium may be used alone or in combination. Preferably, 0.15 g of sodium chloride is present in the head space solid-phase microtextraction (HS-SPME) vial. The SPME fiber is preferably present in an amount effective for absorbing at least 90%, preferably 95%, 98%, or 100% of nitrosamines present in the sample.

The HS-SPME vial is then preferably placed in a autosampler tray (e.g., Combi PAL) to perform an automated extraction technique to extract the nitrosamine-containing content from the sample. The autosampler is used also when performing liquid and headspace analysis. Headspace analysis options include Solid Phase Microextraction (SPME) and ITEX (e.g., a type of purge and trap).

The samples are extracted at the headspace of the HS-SPME vial at a temperature in the range of 25-100° C., 55-80° C., 60-75° C., or 64-70° C. for a time period in the range of 10-30 minutes, 12-28 minutes, or 14-26 minutes. Preferably, the samples are extracted at 65° C. for a time period of 20 minutes. The agitation speed of the automated extraction technique is in the range of 350-600 rpm, 400-550 rpm, or 475-525 rpm. Preferably, the agitation speed is 500 rpm.

Following extraction, the SPME fiber is withdrawn into the SPME syringe needle, and/or separated from the water and inserted into a gas-chromatograph (GC) injection port to undergo desorption. Desorption of the analyte is carried out at a temperature in the range of 100-300° C., 175-275° C., or 225-250° C. for a time period in the range of 30 seconds-4 minutes, 1-3.75 minutes, or 2-3.5 minutes. Preferably, desorption is carried out at a temperature of 250° C. for 3 minutes.

Following desorption, the SPME fiber is optionally cleaned by a method of heating at a temperature in the range of 200-350° C., 225-275° C., or 240-270° C. for a time period in the range of 2-10 minutes, 3-9 minutes or 4-8 minutes. Preferably, heating is carried out at a temperature of 250° C. for 5 minutes.

EXAMPLE

Preparation and Analysis of Nitrosamine Content in an Aqueous Solution Using HS-SPME Method Coupled with Gas-Chromatography Mass-Spectrometry A US EPA 8270-standard solution containing 2000 mg/L of four NAs was purchased from sigma-Aldrich (St. Louis, Mo., USA). The mixture contains, N-nitroso-di-n-ethylamine (NDEA), N-nitroso-di-n-propylamine (NDPA), N-nitrosopiperidine (NPIP) and N-nitroso-di-n-butylamine (NDBA) with purity of >99%.

Working standard solutions of 1 mg/L mixture were prepared by appropriate dilution of stock solution in the same solvent (dichloromethane) and stored in darkness at 4° C. HPLC-grade organic solvents were purchased from Merck (Darmstadt, Germany). Sodium hydroxide and hydrochloric acid were obtained from Scharlau Chemie (Barcelona, Spain). Ultrapure water was obtained from a Milli-Q system (Millipore, Bedford, Mass., USA) and used throughout this study. All laboratory glassware were washed with concentrated hydrochloric acid and rinsed with ultrapure water, acetone and dried out in the laboratory oven for 2 h to avoid any contamination.

SPME fibers coated with polydimethylsiloxane-divinylbenzene (PDMS-DVB, 65-μm), polydimethylsiloxane (PDMS, 100-μm) and polyacrylate (PA, 85-μm) coated fibers were purchased from Supelco (Supelco, Bellefonte, Pa., USA) and used to extract the volatile NAs from water sample. The fibers were conditioned prior to use according to the instructions provided by the suppliers.

Groundwater samples were collected in pre-cleaned glass bottles from four different sources (Hafr Al-Batin, Ras Tanura, Riyadh and Al-Khafji) in Saudi Arabia. Water samples were stored in an ice box and transported to the laboratory. Samples were directly extracted using HS-SPME without any further pretreatment.

Analyses were performed using a gas chromatograph (Agilent technologies, 7890A GC) coupled with a quadrupole mass selective spectrometer (Agilent technologies, 5975C) equipped with an inert ion source and provided with a split-splitless injection port. An A HP-5 GC fused silica capillary column (Agilent 19091J-413; 30 m×320 μm ID×0.25 μm thickness) was selected to separate the analytes. CombiPAL autosampler (GC sampler 80, Zwingen, Switzerland) was used for the automated HS-SPME. Ultrahigh purity helium (99.999%, Abdulah Hashim, Al-Khobar, Saudi Arabia) was used as the carrier gas at a flow rate of 1.0 mL/min. The samples were injected in the splitless mode. The temperature program used for the analyses was as follows: the initial temperature was 40° C. held 3 min which was then increased to 180° C. at 15° C./min and held for 2 min. The total run time was 14.5 min. The injection port, ion source and interface temperatures were 200° C., 200° C., and 280° C., respectively. For qualitative determinations, the MSD was operated in full-scan mode from m/z 50 to 550 and selective ion monitoring mode was used for the quantitative quantification of the analytes.

A 5 mL of water sample (adjusted to pH 7) spiked with NAs was poured into a 10 mL HS-SPME vial containing 0.15 g of sodium chloride and placed in the CombiPAL autosampler tray. Extraction conditions were programmed for automated extraction. Samples were extracted at headspace of the vial at 65° C. for 20 min with 500 rpm agitation speed. After extraction, the SPME fiber was withdrawn into the SPME syringe needle and inserted into the GC injection port for desorption. The desorption was conducted at 250° C. for 3 min and then the SPME fiber was cleaned by heating at 250° C. for 5 min prior to the next extraction. The entire HS-SPME extractions procedure was automated by CombiPAL autosampler.

A multi-variate statistical modeling technique RSM was used to evaluate the response of various HS-SPME parameters. Extraction peak areas ($PA_i$) of NAs influenced by several independent variables such as extraction time (A), sample pH (B), incubation temperature (C) and salt addition (D) (input variables) were used to plot RSM. The proposed RSM required less number of samples analyses when compared to other modeling procedures such one-variable-at-a-time technique. In addition, the design provides curvature (i.e. non-linear behaviors of response surface) in the response function which cannot be achieved in one-variable-at-a-time approaches. Using RSM, the effect of four different parameters (A-D) was investigated to achieve higher extraction efficiency of automated-HS-SPME.

A Box-Behnken design (BBD) with response surface method was employed for developing second order quadratic models with the aid of statistical package Design Expert 8.0 (Stat-Ease, Inc. Minneapolis, Minn.). As the BBD is an orthogonal design, factor levels are evenly spaced and coded for low, medium (central point) and high level, as −1, 0 and +1, respectively, code values were calculated as per eq 1. Table 1 shows the coded values of four variables used for method optimization. A total of twenty five (25) experimental runs were used for implementing the BBD. Each of the twenty five runs was repeated three times and their average were used for the optimization.

$$x_i = \frac{X_i - (X_{high} - X_{low})/2}{(X_{high} - X_{low})/2} \quad (1)$$

where $x_i$ is the coded value and $X_i$ is the original value.

Table 1 is shown below.

| | | | Coded and actual level | | |
|---|---|---|---|---|---|
| Variable | Component | Unit | −1 | 0 | +1 |
| A | Extraction time | min | 20 | 35 | 50 |
| B | PH | — | 3.5 | 7 | 10.5 |
| C | Incubation temperature | ° C. | 50 | 65 | 80 |
| D | Salt addition | % (g/mL) | 0 | 15 | 30 |

Behaviors of the mathematical response models were generally represented by the following quadratic function $$y = \beta_0 + \sum_{i=1}^{k} \beta_i x_i + \sum_{i=1}^{k} \beta_i x_i^2 + \sum_{i=1}^{k-1}\sum_{j=2}^{k} \beta_{ij} x_i x_j + \varepsilon \quad (2)$$

Where y is the predicted response, $\beta_0$ the constant coefficient, $\beta_i$ the linear coefficients, $\beta_{ij}$ the interaction coefficients, $\beta_{ii}$ the quadratic coefficients and $x_i$, $x_j$ are the coded values of the independent variables.

The initial studies were conducted to select the suitable SPME fiber for the extraction of NAs. Three commercially available SPME-fibers with different properties (65-μm polydimethylsiloxane/divinylbenzene (PDMS-DVB), 85-μm polyacrylate (PA) and 100-μm Polydimethylsiloxane (PDMS) fibers) were evaluated. The PA fiber showed higher peak areas for the extraction of NDPA and NDBA in comparison with the PDMS-DVB and PDMS. Polarity of PA fiber with polar-polar interactions facilitates the higher extraction performance of NAs as shown in FIG. 1. FIG. 1 is a graph of the comparison of different SPME fibers. (Conditions: 5 mL of groundwater spiked with 1 mg/L of NAs, agitation speed of 500 rpm; incubation temperature at 50° C. and extraction time for 20 min).

The experimental data of the PA, for the NAs were fitted to eq 2 to develop second order quadratic model which is capable of explaining the main and different degrees of interactive effects on the extraction conditions. The Design Expert 8.0 also gives the analysis of variance (ANOVA) and estimated the coefficient parameters of the regression for the model. The quality of the developed quadratic model was further improved by dropping insignificant interaction effects that dwindle the respective response prediction accuracy. The repeatability of the experimental runs was measured by relative standard deviations (% RSDs) which are ranging between 1.8 and 14.7%. These data were subjected to multiple nonlinear regressions using Design Expert 8.0. The reduced models in terms of coded factors are written in eqs 3 to 6 for NDEA, NDPA, NPIP and NDBA, respectively.

$$PA_{NDEA} = 2364 - 202A - 323B + 68C + 719D + 1147AB - 951AC - 1402AD - 903BC - 2230BD - 1080A^2 - 4B^2 + 2064C^2 + 2675D^2 + 568A^2B - 638A^2C - 2028A^2D - 638AC^2 - 878B^2C + 6042A^2B^2 + 4284A^2D^2 \quad (3)$$

$$PA_{NDPA} = 2.86E+5 - 10515A - 1.1E+5B + 25516C - 29499D - 1.1E+5AB + 1.8E+5AD + 1.23E+5BC + 26855BD + 1.7E+5CD + 1385B^2 - 7651D^2 + 1.1E+5AB^2 + 66567AD^2 - 1.6E+5B^2C + 1.8E+5B^2D + 84338BD^2 \quad (4)$$

$$PA_{NPIP} = 56017 - 9552A - 227B + 24380C + 2155D + 4162AB + 24465AC + 2900AD - 3E + 5BC - 3821BD - 4087CD - 13427A^2 - 31815W - 9157C^2 \quad (5)$$

$$PA_{NDBA} = -1.4E+5A + 1.4E+6B + 6.7E+4C + 2E+5D - 1.3E+7AB + 1.4E+5AC - 1.1E+5AD - 1.6E+6BC - 1.1E+7BD + 1.1E+6CD + 9.5E+6A^2 + 5.8E+6B^2 - 5.4E+6C^2 + 8.17E+6D^2 - 1.5E+7A^2B - 9.8E+5A^2C + 1.5E+7A^2D + 1.3E+7AB^2 + 5E+5B^2C \quad (6)$$

Where $PA_i$ is peak area; NDEA, NDPA, NPIP and NDBA are the NAs compounds.

The coefficients of all variables of the second-order equations provided a measure of the effect on the independent variable of the response ($PA_i$). In addition, positive and negative coefficients values indicate a synergistic and antagonistic effect between the corresponding linear or interactive effect of the response (Ahmadi, M., Vahabzadeh, F., Bonakdarpour, B., Mofarrah, E., Mehranian, M., J. Hazard. Mater. 2005, B123, 187-195—incorporated herein by reference in its entirety). Quality of the developed HS-SPME quadratic model was evaluated based on statistical test of hypothesis. As displayed in Table 2, the models' second-order regression coefficients ($R^2$) are 0.991, 0.788, 0.868 and 0.985 for $PA_{NDEA}$, $PA_{NDPA}$, $PA_{NPIP}$ and $PA_{NDBA}$, respectively.

Table 2 is shown below.

| Precision | $PA_{NDEA}$ ($R^2 = 0.991$) 18.88 | | $PA_{NDPA}$ ($R^2 = 0.788$) 5.801 | | $PA_{NPIP}$ ($R^2 = 0.868$) 5.325 | | $PA_{NDBA}$ ($R^2 = 0.985$) 7.808 | |
|---|---|---|---|---|---|---|---|---|
| | F-value | p-value[a] | F-value | p-value[a] | F-value | p-value[a] | F-value | p-value[a] |
| Model | 22.74 | 0.0040* | 2.88 | 0.0388* | 2.02 | 0.026* | 3.52 | 0.039* |
| A | 1.03 | 0.0368* | 2.39 | 0.0146* | 2.27 | 0.020* | 0.0041 | 0.009* |
| B | 2.63 | 0.0180* | 5.62 | 0.0339* | 0.077 | 0.097** | 0.0094 | 0.008* |
| C | 16.55 | 0.0820** | 0.63 | 0.0442* | 11.03 | 0.029* | 0.093 | 0.081** |
| D | 13.01 | 0.0226* | 1.19 | 0.0295* | 0.1 | 0.076** | 0.009 | 0.009* |

[a]*Significance was established at p < 0.05,
**Significance was established at p < 0.1

An $R^2$ value close to unity, indicates the model's accuracy and good prediction capabilities of the developed models (Kim, J. W., Mazza, G., J. Agric. Food Chem. 2009, 57, 1805-1813—incorporated herein by reference in its entirety). Moreover, all the sources of variations of the four models F-values determined from ANOVA indicated that the models are statistically significant at 5% significant level (i.e at probability values p<0.05). This also further supports the fact that the four equations can adequately predict the best experimental results with high degree of accuracy (Kim, J. W., Mazza, G., J. Agric. Food Chem. 2006, 54, 7575-7584—incorporated herein by reference in its entirety). Similarly, the respective p-values established at either 5% or 10% significant level (i.e p<0.05 or p<0.1) suggest that the investigated parameters are influencing the extraction method. In addition, the adequate precision (measure of signal to noise ratio) for all the models are shown in Table 3.

Considering the main factors, the coefficients of the independent variables of A and B were negative for all NAs except NDBA (eq 6). The other two independent variables C and D were in positive for all NAs except the coefficient of variable D for NDPA (eq 4). This implies that lower level of A and B, and higher level of C and D are expected to give higher $PA_i$. In this regard, the relative contributions of the main effects on the extraction of NAs from groundwater could be ranked according to the order of salt addition>incubation temperature>absorption time>pH, respectively.

Three-dimensional response surface curves for the PA; quadratic models were constructed. This enables more clear visualization and understanding the influence of the independent variables. Each of the response curves was developed by fixing two of the independent variables while varying the remaining two within the investigated range. For example, in FIG. 2 the variable are extraction time and sample pH (incubation temperature and salt additions were kept constant). These curves corroborate the ANOVA analysis and revealing the independent variables which have significant contributions on the HS-SPME response.

FIG. 2A-FIG. 2D shows an increase response of NDEA, NDPA and NDBA by increasing extraction time, whereas for NPIP, the maximum response was observed after 35 min extraction time. Furthermore, stronger degree of curvature is due to influence of sample pH (B) which is portrayed in the upward plateau shape (FIG. 2A-FIG. 2D) and reach maximum around pH 9.5 and then decreases. This could be due to hydrolysis of the NAs at high alkaline conditions (pH 10.5) as shown in FIG. 2A-FIG. 2D. FIG. 2A-FIG. 2D are graphs of the extraction time and sample pH on HS-SPME. (Conditions: 5 mL of groundwater spiked with 50 µg/L of NAs, agitation speed of 500 rpm; incubation temperature at 65° C. and salt addition 15%).

FIG. 3A-FIG. 3d are graphs of the effect of sample pH and salt addition on HS-SPME. (Conditions: 5 mL of groundwater spiked with 50 µg/L of NAs, agitation speed of 500 rpm; extraction time 35 min and incubation temperature at 65° C.). In FIG. 3A-FIG. 3D the variable are sample pH and the influence of salt addition (extraction time and incubation temperature were kept constant). At fixed central value of A and C the extraction performance of HS-SPME is shown in FIG. 3a-FIG. 3D. The PA; of all NAs were increases with increasing amount of salt addition. Interestingly, at alkaline conditions in the presence of salt decreases the hydrolysis rate of NDEA and NDBA. Reverse effect for NDPA was observed by increasing sample pH higher than 7.5. From this (FIG. 3A-FIG. 3D) NDPA and NPIP were degraded at alkaline conditions in presence of salt (Aristidi, N. A., Kallirroy-Ioanna, G. L., Talanta 2009, 79, 86-91—incorporated herein by reference in its entirety).

Figure 4A:
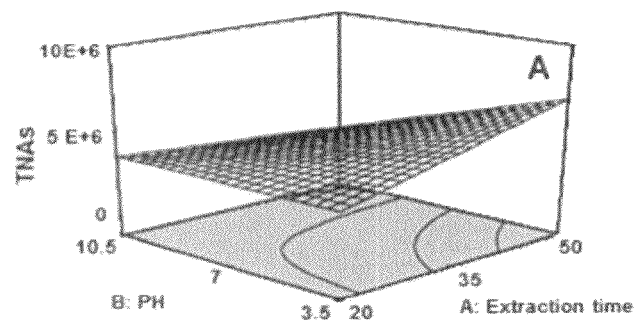
FIGS. 4A-4D are diagrams that illustrate the effect of incubation temperature and salt addition on HS-SPME.

FIG. 4A-4D are graphs of the effect of incubation temperature and salt addition on HS-SPME. (TNAs: sum of NDEA, NDPA, NPIP and NDBA) (Conditions: 5 mL of groundwater spiked with 50 µg/L of NAs, agitation speed of 500 rpm; extraction time 35 min and sample pH 7). FIG. 4A-FIG. 4D displays the influence of HS-SPME conditions with respect to total nitrosamines (TNAs) response. FIG. 4A, extraction time and sample pH are the variables and incubation temperature and salt concentrations were maintained as constant. Results clearly indicate that TNAs increases with increasing extraction time and no significant improvement of TNAs were observed with change in sample pH.

Figure 4B:
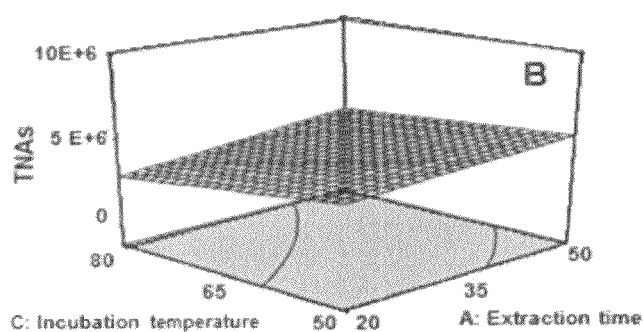

FIG. 4B shows the relationship between extraction time and incubation temperature. Increasing the extraction time increases the efficiency of HS-SPME. However, after 65° C. a slight decrease in TNAs was observed.

Figure 4C:
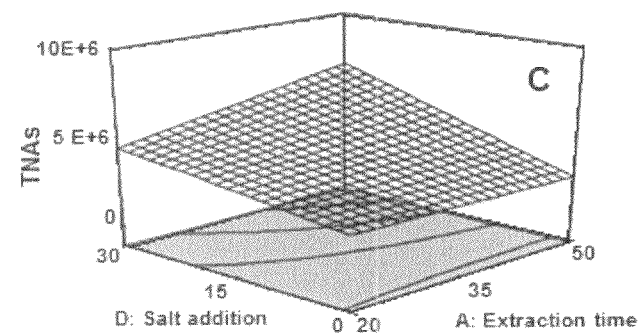
Figure 4D:
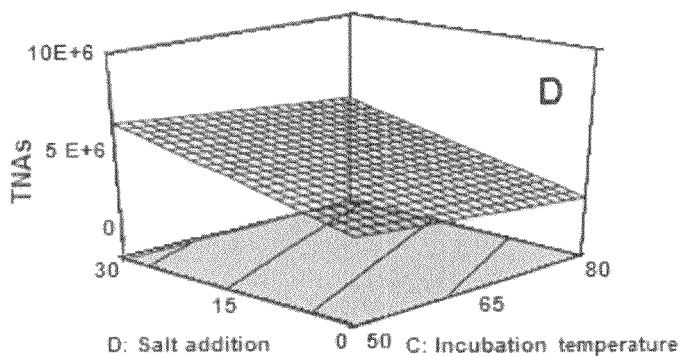

FIG. 4C shows the influence of salt addition on extraction time and the FIG. 4D displays the effect of salt addition on incubation temperature while other experimental conditions were kept constant. Results clearly indicate that extraction time and incubation temperature are not significantly influence the HS-SPME by the additions of salt. The salt addition (D) had positive effect on the extraction of TNAs; these findings are in agreement with previously report HS-SPME method.

Figure 5:
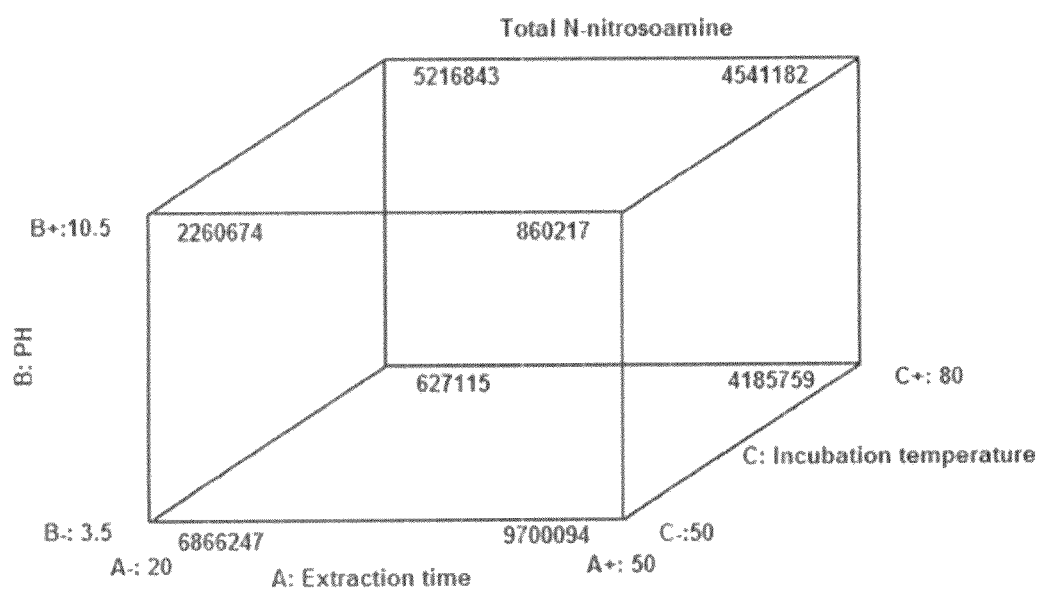
FIG. 5 illustrates the influence of extraction time, sample pH and incubation temperature on HS-SPME.
Figure 6:
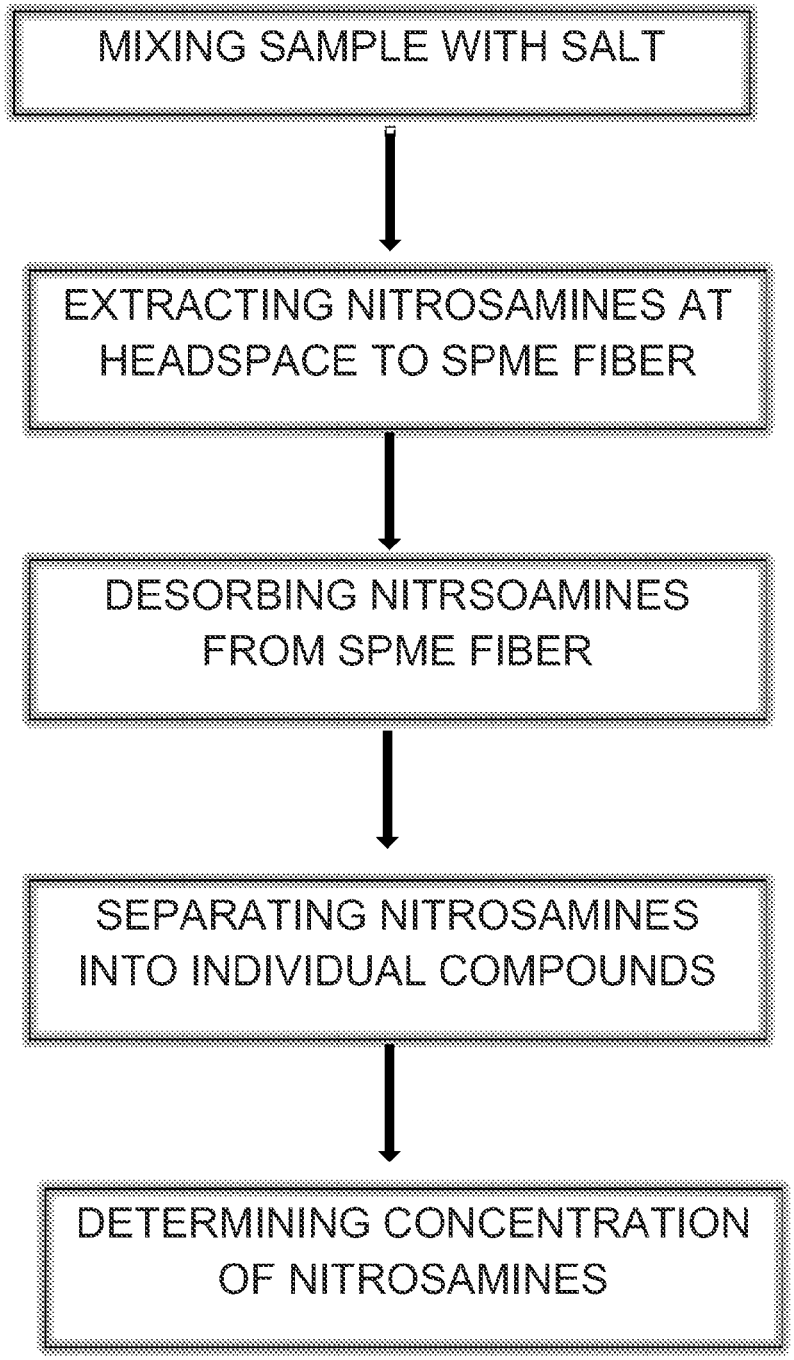
FIG. 6 is a flowchart illustrating an automated method for determining nitrosamine concentration in an aqueous sample by headspace solid-phase microextraction gas chromatography-mass spectrometry according to one embodiment.

The results of ANOVA and RSM showed that among tested variables, salt additions (D) were the most important variable in the extraction of NAs with HS-SPME. Thus, the influences of other three independent variables (A, B and C) on HS-SPME were studied with known amount of salt addition (i.e. 15%) and illustrated in a cube plot as shown in FIG. 5. FIG. 5 illustrates the influence of extraction time, sample pH and incubation temperature on HS-SPME. (Conditions: 5 mL of groundwater spiked with 50 µg/L of NAs, agitation speed of 500 rpm and 15% Salt addition). Each cube corner represents the eight different experimental conditions with the coded levels from −1 to +1. The highest peak areas of TNAs (9.7 E+6) was obtained for the combination of a high extraction time (+A) and moderate pH (−B) with moderate incubation temperature (−C) at fixed salt addition 15%.

Thus, the forgone analyses imply that among the four NAs investigated, NDEA is the least favorable for extraction in the water sample using HS-SPME (FIG. 2A-FIG. 2D and FIG. 3A-FIG. 3D). Based on the model, the order of influencing HS-SPME parameters are ranked in the order of D>C>A>B, respectively.

The optimum conditions for the extraction of individual and TNAs were predicted using coded values of the independent variables. With least parameters (i.e., 3 parameters) under investigation, finding the optimum region through visual inspection of the response surfaces is possible in absence of constraints. However, for higher number of parameters (as in the case of present study), obtaining the global (rather than local) maximum point is a challenging task. As such, simultaneous numerical optimization for the extraction was performed with the aid of the Design-Expert@ 8.0. The coordinates of the optimal points were calculated through equating the first derivatives of the reduced models (eqs 3 to 6) to zero according to eq 7 in conjunction with set of convergent criteria (Bezerra, M. A., Santell, R. E., Oliveira, E. P., Villar, L. S., Escaleira, L. A., Talanta, 2008, 76, 965-977; Anderson, M. J., Whitcomb, P. J., "RSM simplified: Optimizing Processes Using Response Surface Methods for Design of Experiments," 2005, Productivity Press, New York—each incorporated herein by reference in its entirety). The convergent criteria are composed of goals based on desired constraints for the parameters of interest (responses and the independent variables). The criteria weighted the individual parameters to their relative importance in contributing towards the desired targeted goals.

$$\frac{\partial y}{\partial x_i} = \beta_i + 2\beta_{ii}x_i + \sum_{j=2}^{k} \beta_{ij}x_j + \ldots = 0 \quad (7)$$

Using ANOVA program, optimum conditions were identified to enhancing the performance of HS-SPME. The highest extraction of NAs in water samples were as follows; 20 min extraction time, sample pH of 7, 65° C. incubation temperature and 30% salt addition. Further more the desirability of these optimization value was 0.968.

Based on the optimized conditions, quantitative parameters of HS-SPME such as linearity, repeatability and limits of detection (LODs) were investigated. The results are summarized in Table 3 shown below.

| Analytes | linearity equation | (correlation of coefficient R) | Linear range (μg/L) | % RSDs (n = 3) | LODs (ng/L) |
|---|---|---|---|---|---|
| NDEA | y = 0.0006x + 7.6642 | 0.975 | 0.1-100 | 3.8 | 11.9 |
| NDPA | y = 5E−05x + 6.6024 | 0.988 | 0.1-100 | 5.7 | 9.6 |
| NPIP | y = 0.0005x + 7.7974 | 0.977 | 0.1-100 | 3.5 | 5.4 |
| NDBA | y = 8E−06x + 0.0614 | 0.992 | 0.1-100 | 1.8 | 0.78 |

Linearity was tested over the concentration range of 0.1 to 100 μg/L (0.1, 1, 5, 10, 20, 30, 50, 100 μg/L) for all NAs and very good correlation of coefficient (R) ranging from 0.975 to 0.992. The repeatability study was carried out by extracting spiked water samples at a different concentration levels and the percentage relative standard deviations (% RSDs) were between 1.8 and 5.7% (n=3). The LODs, based on a signal-to-noise ratio (S/N=3), were ranged from 0.78 to 11.9 ng/L. Performance of automated HS-SPME was compared with other methods reported in the literatures and the results are shown in Table 4 shown below.

| Method | Sample | Linear range (ng/L) | LODs (ng/L) | % RSDs | Ref- |
|---|---|---|---|---|---|
| SPE/GC-EI-MS-MS[a] | Water | 500-50000 | 0.4-4 | max 10 | [Donald, et al.] |
| HS-SPME/GC-MS-MS[b] | Water | 10-1500 | 1-5 | 3-13.0 | [Llop, et al.] |
| HPLC-CL[c] | Water | 5-1000 | 1.5-3 | 0.7-4.5 | [Kodamatani, et al.] |
| SPE/GC-FID[d] | Water | 10000-600000 | 2000-3500 | 3-6.5 | [Sanchez, et al.] |
| SPE/GC-NPID[e] | Water | 300-20000 | 20-80 | 3.5-6.3 | [Sanchez, et al.] |
| SPE/GC-MS | Water | 40-20000 | 3-13.0 | 4.1-6.1 | [Sanchez, et al.] |
| HS-SPME/GC-MS | Water | 100-100000 | 0.8-11.9 | 1.8-5.7 | Present |

Donald, et al. refers to (Donald, J. A., Harden, N. B., Nghiem, L. D., Khan, S. J., Talanta 2012, 99, 146-154—incorporated herein by reference in its entirety).
Llop, et al. refers to (Llop, A., Borrull, F., Pocurull, E., J. Sep. Sci. 2010, 33, 3692-3700—incorporated herein by reference in its entirety).
Kodamatani, et al. refers to (Kodamatani, H., Yamazaki, S., Saito, K., Karikari, A. A., Kishikawa, N., Kurodad, N., Tomiyasu, T., Komatsu, Y., J. Chromatogr. A 2009, 1216, 92-98 incorporated herein by reference in its entirety).
Sanchez, et al. referes to (Sanchez, B. J., Ballesteros, E., Gallego, M., J. Chromatogr. A 2007, 1154, 66-73—incorporated herein by reference in its entirety).

Results of NAs clearly indicate that the performance of HS-SPME is comparable with those reported SPME-GC-MS-MS methods and superior to SPE-GC-MS methods (Table 4). One advantage of this method is simple and the entire extraction process was automated which minimize the experimental errors.

The automated HS-SPME-GC-MS method was applied to determine the NAs in groundwater samples at different locations of Saudi Arabia (Hafr Al-Batin, Ras Tanura, Riyadh and Al-Khafji). The concentrations of NAs that detected in groundwater samples are shown in Table 5 shown below.

| Concentration of N-nitrosamine in groundwater samples (μg/L) (n = 4) | | | | | | | |
|---|---|---|---|---|---|---|---|
| Analytes | Hafr Al-Batin | % RSDs | Ras Tanura | % RSDs | Riyadh | % RSDs | Al-Khafji | % RSDs |
| NDEA | 13.27 | 1.06 | 14 | 0.70 | 15.24 | 1.33 | 14.67 | 1.66 |
| NDPA | 7.67 | 0.80 | 7.9 | 0.70 | 7.97 | 0.80 | 7.5 | 1.23 |
| NPIP | 9.07 | 1.15 | 8.49 | 1.07 | 8.9 | 0.70 | 8.27 | 0.39 |
| NDBA | 0.15 | 0.01 | 0.31 | 0.03 | 0.32 | 0.03 | 0.32 | 0.04 |

To assess the matrix effect of the HS-SPME, groundwater samples were spiked with 1 and 20 μg/L of NAs and extraction recoveries were calculated. Recoveries of NAs in different groundwater samples were shown in Table 6. Moreover, matrix effects were not a significant factor, with analyte recoveries in the range of 85 and 114% and suitable for routine analyses of NAs in groundwater samples.

Table 6 is shown below.

| | Recoveries of NAs at 20 μg/L spiked real water samples (n = 4) | | | | | | | |
|---|---|---|---|---|---|---|---|---|
| Analytes | Hafr Al-Batin PH = 8.5 | % RSDs | Ras Tanura PH = 7.98 | % RSDs | Riyadh PH = 7.95 | % RSDs | Al-Khafji PH = 9.25 | % RSDs |
| NDEA | 89 | 4.6 | 91 | 2 | 103 | 5.2 | 89 | 8.4 |
| NDPA | 112 | 8 | 112 | 2 | 107 | 4.6 | 109 | 0.8 |
| NPIP | 96 | 1.3 | 101 | 6 | 114 | 4.1 | 88 | 5.2 |
| NDBA | 103 | 15 | 106 | 5 | 110 | 3.7 | 106 | 2 |

| | Recoveries of NAs at 1 μg/L spiked real water samples (n = 4) | | | | | | | |
|---|---|---|---|---|---|---|---|---|
| | Hafr Al-Batin | % RSDs | Ras Tanura | % RSDs | Riyadh | % RSDs | Al-Khafji | % RSDs |
| NDEA | 85 | 4.1 | 92 | 4.8 | 99 | 8.3 | 92 | 3 |
| NDPA | 102 | 3.7 | 104 | 9.6 | 94 | 1.2 | 98 | 1.7 |
| NPIP | 105 | 3.8 | 97 | 5.7 | 102 | 6.6 | 92 | 1.5 |
| NDBA | 96 | 5.4 | 101 | 4.1 | 94 | 4.9 | 91 | 1.97 |

An automated HS-SPME-GC-MS method was developed to the determination of N-nitrosamine in groundwater samples. The extraction conditions of HS-SPME were modeled via response surface methodology. With the use of an autosampler very good detection limits (between 0.79 and 11.9 ng/L) were obtained and satisfactory precision (between 1.8-5.7%). The fully automated method proved to be simple and viable approach for trace level determining NAs in groundwater samples.

In one embodiment of the invention no derivatization of the nitrosamine content is required, e.g., without denitrosation and/or without sulfonylation. The nitrosamine content is determined directly without prior chemical modification of the nitrosamine.

In one embodiment of the invention automated headspace analysis method is used as a gas chromatographic technique.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The invention claimed is:

1. An automated headspace solid-phase microextraction gas chromatography-mass spectrometry method for determining nitrosamine concentration, comprising:

mixing a nitrosamine-containing aqueous sample that has not been pretreated with one or more salts in a vial comprising an SPME fiber at a headspace portion above the unfiltered nitrosamine-containing aqueous sample in the vial;

extracting a nitrosamine-containing analyte from the nitrosamine-containing aqueous sample with the SPME fiber at the headspace portion at 60-75° C. for 15-25 minutes;

desorbing the nitrosamine-containing analyte from the SPME fiber in an injection port of a gas chromatograph coupled with a single mass spectrometer comprising only a single mass separation step at 225-250° C. for 2-3 minutes; and separating the nitrosamine-containing analyte in the gas chromatograph coupled with the single mass spectrometer into a plurality of individual nitrosamine compounds; and determining the nitrosamine concentration in the nitrosamine-containing analyte with the single mass spectrometer;

wherein the nitrosamine-containing aqueous sample comprises a total original nitrosamine concentration of 30-35 μg/L before the nitrosamine-containing aqueous sample is spiked with 20 μg/L of nitrosamine such that the extracting comprises and maintains an analyte recovery rate of at least 85% and up to 114%.

2. The method of claim 1, wherein the SPME fiber is a 85 μm polyacrylate fiber.

3. The method of claim 1, wherein the nitrosamine present in the nitrosamine-containing aqueous sample is not derivatized.

4. The method of claim 1, wherein the unfiltered nitrosamine-containing aqueous sample comprises one or more nitrosamine compounds selected from the group consisting of N-Nitrosodiethylamine (NDEA), N-Nitrosodi-n-propylamine (NDPA), N-Nitrosopiperidine (NPIP) and N-Nitrosodi-n-butylamine (NDBA).

5. The method of claim 1, wherein the extracting is carried out at 63-65° C. for 18-20 minutes.

6. The method of claim 1, wherein the desorbing is carried out at 240-250° C. for 2-3 minutes.

7. The method of claim 1, wherein the extracting further comprises agitation at 475-500 rpm.

8. The method of claim 1, wherein the unfiltered nitrosamine-containing aqueous sample is mixed with the one or more salts to a final salt concentration of 15%-30%.

* * * * *